(12) United States Patent
Shaw et al.

(10) Patent No.: US 7,125,902 B2
(45) Date of Patent: Oct. 24, 2006

(54) METHODS, COMPOUNDS, AND DIAGNOSTICS FOR CANCER TREATMENT

(75) Inventors: Jiajiu Shaw, Ann Arbor, MI (US); An-Rong Lee, Taipei (TW); Wen-Hsin Huang, Taipei (TW)

(73) Assignee: Unitech Pharmaceuticals, Inc., Ann Arbor, MI (US)

( * ) Notice: Subject to any disclaimer, the term of this patent is extended or adjusted under 35 U.S.C. 154(b) by 61 days.

(21) Appl. No.: 10/856,519

(22) Filed: May 28, 2004

(65) Prior Publication Data

US 2005/0267175 A1    Dec. 1, 2005

(51) Int. Cl.
*A61K 31/42* (2006.01)
(52) U.S. Cl. ..................................... 514/378
(58) Field of Classification Search ................. 514/378
See application file for complete search history.

(56) References Cited

U.S. PATENT DOCUMENTS 5,721,277 A    2/1998   Tang
5,760,066 A    6/1998   Tang
5,977,151 A    11/1999  Mullner et al.
6,727,272 B1   4/2004   Lee et al.

OTHER PUBLICATIONS

Freshney (Culture of Animal Cells, A Manual of Basic Technique, Alan R. Liss, Inc., 1983, New York, p. 4.*
Dermer (Bio/Technology, 1994, 12:320).*
Verma et al. (Nature 1997; 389, 239-242).*
Marshal (Science 1995; 269 (5227): 1050-1055.*
Eck et al. (Goodman & Gilman's The Pharmacological Basis of Therapeutics (1996), 9$^{th}$ Edition, Chapter 5, McGraw-Hil, NY).*
Juengst (British Medical Journal 2003: 326, 1410-1411.*
Rubanyi (Mol. Aspects Med. 2001; 22; 113-142).*
Ross et al., Human Gene Therapy, 1996, vol. 7, pp. 1781-1790.*

* cited by examiner

*Primary Examiner*—Kamal A. Saeed
*Assistant Examiner*—Jason M. Nolan
(74) *Attorney, Agent, or Firm*—Brinks Hofer Gilson & Lione; Gregory H. Zayia

(57) ABSTRACT

Methods of treating cancer employing isoxazole derivatives are described. Compounds and methods of using these compounds for isolating and/or detecting binding proteins, which may be indicative of a disease, are also described.

5 Claims, 1 Drawing Sheet

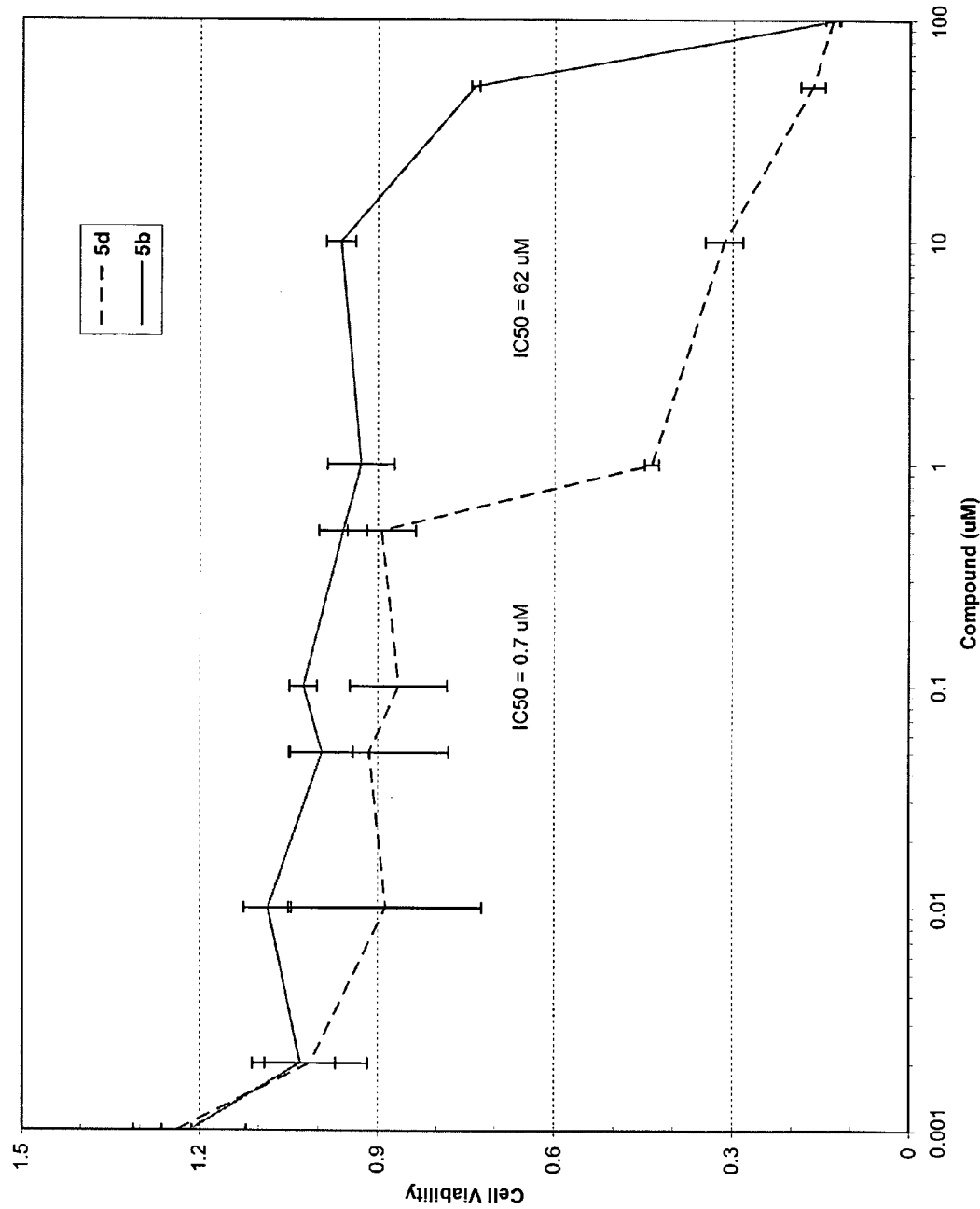

METHODS, COMPOUNDS, AND DIAGNOSTICS FOR CANCER TREATMENT

BACKGROUND

Leflunomide, N-(4-trifluoromethylphenyl)-4-carboxamidyl-5-methylisoxazole, is an isoxazole derivative developed by Aventis Pharmaceuticals for treating Rheumatoid Arthritis that was recently introduced on the market:

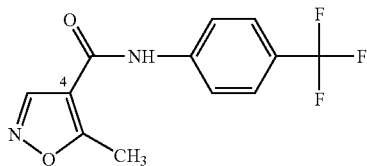

Leflunomide

Recently, leflunomide and some of its analogs were tested for several cancer cell lines as described in U.S. Pat. No. 5,977,151. This work claims that certain leflunomide analogs can be used to treat lung cancer, leukemia, Kaposi's sarcoma, ovarian cancer, sarcoma, meningioma, intestinal cancer, cancer of the lymph nodes, brain tumors, breast cancer, stomach cancer, cancer of the pancreas, cancer of the prostate, and skin cancer.

However, leflunomide is known for its toxic side effects, such as hepatotoxicity and lymphoma. For example, leflunomide has caused 12 deaths by liver failure in the U.S. and 5 deaths by intestinal pneumonia in Japan. Thus, as a therapeutic agent for cancer treatment, leflunomide could be significantly improved.

SUMMARY

The scope of the present invention is defined solely by the appended claims, and is not affected to any degree by the statements within this summary.

A method for treating cancer embodying features of the present invention includes administering to a patient or an animal in need thereof a therapeutically effective amount of a compound having a formula (I):

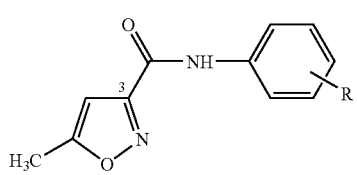

or a physiologically tolerable salt thereof. In formula (I), R is selected from the group consisting of —H, 2-Cl, 3-Cl, 4-Cl, 2,4-(Cl)$_2$, 2-F, 3-F, 4-F, 2,4-(F)$_2$, 2-Br, 3-Br, 4-Br, 2,4-(Br)$_2$, 2-CF$_3$, 3-CF$_3$, 4-CF$_3$, 2,4-(CF$_3$)$_2$, 2-COOH, 3-COOH, 4-COOH, 2,4-(COOH)$_2$, 2-OCH$_3$, 3-OCH$_3$, 4-OCH$_3$, 3,4,5-(OCH$_3$)$_3$, 2-NH—CO—CH$_2$Cl, 4-NH—CO—CH$_2$Cl, 2-NH—CO—CH$_2$Br, 4-NH—CO—CH$_2$Br, or —CONHCH(COOC$_2$H$_5$)CH$_2$CH$_2$COOC$_2$H$_5$.

A compound embodying features of the present invention has a formula (II):

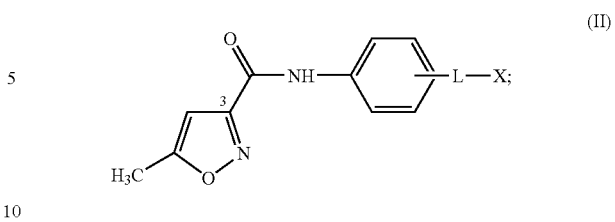

wherein L is a bridging unit, and X is a polymer or solid. In formula (II), -L-X is selected from the group consisting of —O—X, —O—(CH2)n—X, —NH—X, —NH—CO—CH2-X, and —NH—CO—CHR—X. R is a radical of an amino acid and n is 1, 2, 3, 4, or 5.

BRIEF DESCRIPTION OF THE DRAWING

FIG. 1 is a chart showing the effects of UTL-5b and UTL-5d on HT-29 colon cancer cells.

DETAILED DESCRIPTION

The present invention discloses methods and compounds for treating cancer by one or more isoxazole derivatives that may have better efficacy and/or reduced toxicity as compared to leflunomide.

The present invention provides methods of cancer treatment, which include administering one or more isoxazole derivatives in accordance with the present invention to a cancer patient or animal in need thereof. Several isoxazole derivatives discovered by the present inventors have been described in U.S. Pat. No. 6,727,272.

The present invention discloses a method for treating cancer by an isoxazole derivative having a formula (I) or a physiologically tolerable salt thereof:

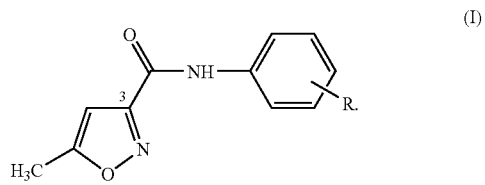

In formula (I), R is —H, 2-Cl, 3-Cl, 4-Cl, 2,4-(Cl)$_2$, 2-F, 3-F, 4-F, 2,4-(F)$_2$, 2-Br, 3-Br, 4-Br, 2,4-(Br)$_2$, 2-CF$_3$, 3-CF$_3$, 4-CF$_3$, 2,4-(CF$_3$)$_2$, 2-COOH, 3-COOH, 4-COOH, 2,4-(COOH)$_2$, 2-OCH$_3$, 3-OCH$_3$, 4-OCH$_3$, 3,4,5-(OCH$_3$)$_3$, 2-NH—CO—CH$_2$Cl, 4-NH—CO—CH$_2$Cl, 2-NH—CO—CH$_2$Br, 4-NH—CO—CH$_2$Br, or —CONHCH(COOC$_2$H$_5$)CH$_2$CH$_2$COOC$_2$H$_5$.

A method of cancer treatment embodying features of the present invention includes administering to a patient or an animal in need thereof a therapeutically effective amount of a compound of formula (I) or a physiologically tolerable salt thereof.

The methods of cancer treatment in accordance with the present invention may further include administering one or more additional cancer therapeutic agents. Representative additional cancer therapeutic agents may include but are not limited to tumor irradiation, an expression construct comprising a nucleic acid encoding a cancer therapeutic gene, and a promoter operative in eukaryotic cells wherein said nucleic acid is operatively linked to said promoter.

A representative chemotherapeutic agent includes but is not limited to a DNA damaging agent. Representative DNA damaging agents include but are not limited to cisplatin, carboplatin, oxaliplatin, taxol, 5-fluorouracil, verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, vincristin, vinblastin, methotrexate, and the like, and combinations thereof.

Representative irradiation includes but is not limited to X-ray radiation, UV-radiation, γ-radiation, microwave radiation, and the like, and combinations thereof.

Representative expression constructs include but are not limited to an adenovirus, an adeno-associated virus, a vaccinia virus, a herpes virus, and the like, and combinations thereof.

Representative nucleic acids include but are not limited to cDNA, genomic DNA, and the like, and combinations thereof.

The nucleic acid encodes a therapeutic gene. Representative therapeutic genes include but are not limited to p53, p16, p21, MMAC1, p73, zac1, C-CAM, BRCAI, Rb, Bax, Bak, Bim, Bik, Bid, Bad gene Harakiri, Ad E1B, an ICE-CED3 protease, a cytokine, and the like, and combinations thereof.

cultured in 90% MEM (Eagle) with non-essential amino acids and Earle's BSS amd 10% FBS.

In Vitro Assay for Cellular Viability (MTT Calorimetric Assay)

All compounds were tested for inhibition of anchorage-dependent tumor cell growth using MTT assay. All compounds were individually solubilized in DMSO and diluted into appropriate growth medium at 2-fold desired final assay concentration. In assays, cells were seeded into 96-well plates and allowed to adhere for 24 h before drugs were introduced. Following a 48-h incubation, compounds and medium were removed by flicking, and each well was treated with 100 μl of 500 μg/ml MTT [3-(4,5-dimethylthiazol-2-yl)-2,5-diphenyltetrazolium bromide] in culture medium. Following a 4-h incubation period to allow metabolism of MTT by mitochondrial dehydrogenases of viable cells to form an insoluble formazan product, the crystals were dissolved in 100 μL of acid-SDS (0.01 N HCl in 10% SDS) by incubating the plate overnight. Absorbance, as a measure of cell viability, was read the following day in an ELISA plate reader at a wavelength of 550 nm. $IC_{50}$ values were obtained by a linear regression analysis of percentage absorbance vs. log drug concentration.

Results on C6 (Rat Glialtumor Cell or CCL-107) Cell Line

| Compound | R | $IC_{50}$ (μM) | Compound | R | $IC_{50}$ (μM) |
|---|---|---|---|---|---|
| Leflunomide | | 0.162 | UTL-5i | 3,4,5-$(OCH_3)_3$ | 1.18 |
| A77 1726 | | 0.159 | UTL-5f | 4-$CF_3$ | 0.17 |
| UTL-5a | 4-H | 1.37 | UTL-5e | 3-$CF_3$ | 0.2 |
| UTL-5c | 3-Cl | 0.163 | UTL-5k | 4-F | >1000 |
| UTL-5d | 4-Cl | 0.81 | UTL-5j | 4-COOH | 0.19 |
| UTL-5g | 2,4-$(Cl)_2$ | 0.18 | UTL-5l | 4-CONHCH(COO$C_2H_5$) $CH_2CH_2COOC_2H_5$ | 0.16 |
| UTL-5h | 4-$OCH_3$ | 0.35 | | | |

As shown below in Example 1 and Example 2, isoxazole derivatives in accordance with the present invention are effective against several different cancer cells in vitro. As shown in example 3, the isoxazole derivatives are shown to have significantly higher $LD_{50}$ values as compared to leflunomide, indicating that these isoxazole derivatives are associated with significantly lower acute toxicity.

The following representative examples and procedures are provided solely by way of illustration, and are not intended to limit the scope of the appended claims or their equivalents.

EXAMPLE 1

In Vitro Anticancer Activity (on C6 and Hep G2 Cells)

Cell Culture

Cell lines (C6 and Hep G2) were obtained from the Bioresource Collection and Research Center. All cell culture media and supplements were purchased from Invitrogen, Co. (GIBCO™, Gland Island, N.Y.) unless otherwise specified. All cells were grown in a humid atmosphere of 95% air and 5% $CO_2$ at 37° C. Cell lines were maintained under standard conditions in culture media recommended by the American Type Culture Collection (ATCC), unless otherwise specified. C6 cells were grown in 82.5% Ham's F-10 medium, 15% horse serum and 2.5% FBS. Hep G2 were

EXAMPLE 2

In Vitro Anticancer Activity (on HT-29 Cells)

Cell Line and Culture Conditions

The cell lines used were HT29 (adenocarcinoma of the colon). The tumor cells were grown at 37° C. in a humidified atmosphere (5% $CO_2$) as monolayer cultures in RPMI 1640 medium supplemented with 10% FCS. Cells were trypsinized upon passage and maintained routinely.

Compounds

UTL-5b and UTL-5 were dissolved in DMSO as 4 mM stock solutions and then further diluted in 1% carboxymethyl cellulose. While UTL-5d was well solubilized, UTL-5b appeared as a suspension and could not be completely dissolved.

SRB Assay

The SRB assay is routinely employed to measure cell proliferation by the US-NCI 60 cell line screen. Exponentially growing cells were harvested by trypsination, counted and seeded into 96 well plates (2.000 cells/well). Compound was added in 8 concentrations ranging from 0.01–100 μM. Total protein mass was determined after 5d of continuous drug exposure by addition of Sulforhodamine B (0.4%) solution. Readings were read at 515 nm, as cell viability, and $IC_{50}$ values were estimated based on the results.

Results (HT-29 Cell Line)

UTL-5b and UTL-5d both were shown with very good activity in the human colon cancer cell line HT29. The cell viability and the $IC_{50}$ values are listed in the following tables and are also shown in FIG. 1.

Cell Viability (UTL-5b treated)

| | Cell Viability (UTL-5b Treated) | | | | | | | | | |
|---|---|---|---|---|---|---|---|---|---|---|
| | Conc. (µM) | | | | | | | | | |
| | 0.001 | 0.002 | 0.01 | 0.05 | 0.1 | 0.5 | 1 | 10 | 50 | 100 |
| Reading (avg of 3) | 1.216 | 1.030 | 1.085 | 0.994 | 1.026 | 0.959 | 0.928 | 0.962 | 0.734 | 0.120 |
| S.D. | 0.095 | 0.059 | 0.040 | 0.053 | 0.023 | 0.040 | 0.057 | 0.025 | 0.007 | 0.000 |

Cell Viability (UTL-5d treated)

| | Cell Viability (UTL-5d Treated) | | | | | | | | | |
|---|---|---|---|---|---|---|---|---|---|---|
| | Conc. (µM) | | | | | | | | | |
| | 0.001 | 0.002 | 0.01 | 0.05 | 0.1 | 0.5 | 1 | 10 | 50 | 100 |
| Reading (avg of 3) | 1.238 | 1.014 | 0.886 | 0.914 | 0.864 | 0.893 | 0.436 | 0.314 | 0.164 | 0.13 |
| S.D. | 0.025 | 0.097 | 0.164 | 0.135 | 0.083 | 0.058 | 0.012 | 0.032 | 0.021 | 0.013 |

$IC_{50}$ (µM) value of UTL-5b and UTL-5d

| $IC_{50}$ (µM) Values of UTL-5b and UTL-5d | | |
|---|---|---|
| Compound | R | $IC_{50}$ (µM) |
| UTL-5b | 3-Cl | 62 |
| UTL-5d | 4-Cl | 0.7 |

EXAMPLE 3

Determination of $LD_{50}$ Values

Leflunomide, its metabolite (A77 1726), and several isoxazole derivatives were chosen for the acute toxicity study. Male ICR mice were used for the intraperitoneal injection of each compound at different doses according to the following procedure: Small male ICR mice are chosen, each weighing 17–23 grams. They are equally classified at random into individual groups, 3–5 mice per group. A predetermined dose of each selected compound in minimum DMSO/liquid paraffin is injected once intraperitoneally to mice in each group. Toxic reaction is observed for three days, then the acute half lethal dose ($LD_{50}$) is determined.

Results

The acute symptoms observed before death included agitation, lacrimation, crawling, trembling, and reduced motility. Cyanosis and deep necrosis as well as the above-described acute symptoms were noticed at death in mice that received leflunomide and A77 1726 between 1 and 12 hr after dosing. For 5a, 5b, 5g, and 5j, all mice were alive at 2,000 mg/Kg. No further attempts were made to determine the $LD_{50}$. The only acute symptom in these mice challenged by these four compounds at 2,000 mg/Kg was "agitation" observed in day one during the three-day observation. $LD_{50}$ values determined for each compound studied are shown in the following table.

| $LD_{50}$s (mg/Kg) of the selected compounds | | | | | |
|---|---|---|---|---|---|
| Compound | R | $LD_{50}$ (mg/Kg) | Compound | R | $LD_{50}$ (mg/Kg) |
| Leflunomide | | 250 | A77 1726 | | 200 |
| UTL-5a | 4-H | >2,000 | 5g | 2,4-(Cl)$_2$ | >2,000 |
| UTL-5b | 2-Cl | >2,000 | 5j | 4-COOH | >2,000 |
| UTL-5d | 4-Cl | 1,800 | | | |

The present invention also discloses an isoxazole derivative having a formula (II):

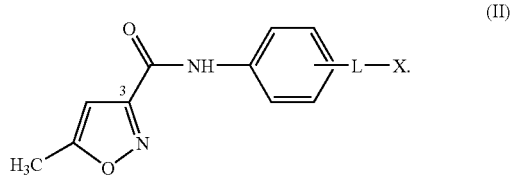

In formula (II), L is a bridging unit, X is a polymer or solid, and -L-X is selected from the following groups: (a) —O—X; (b) —O—(CH$_2$)$_n$—X in which n is 1, 2, 3, 4, or 5; (c) —NH—X; (d) —NH—CO—CH$_2$—; and (e) —NH—CO—CHR—X in which R is a radical of an amino acid. The radical "-L-X" in formula (II) may be in the ortho-, meta-, or para-position relative to the "NH" group on the phenyl ring, and preferably in the para-position. The term "polymer" refers to a natural or synthetic polymer. Representative polymers include but are not limited to polyvinyl chloride, polyethylene, polystyrene, polypropylene, polysaccharide, Sepharose, protein, peptide, lipid, silicate, nucleic acid, and the like, and combinations thereof. The polymer optionally provides one or more of functional groups including but not limited to —OH, —COOH, —NH₂, —CO—, and the like, and combinations thereof, in order that they may be coupled to the bridging unit L. The term "solid" refers to insoluble materials including but not limited to particulates, beads, microtiter plates, and the like, and combinations thereof.

The compounds of formula (II) are also suitable for finding specific binding proteins in biological fluids such as blood, urine, serum, cell extract, synovial fluid, and the like. Methods in accordance with the present invention may be used for the modification of microtiter plates, for the purification of proteins or peptides, for the preparation of chromatographic material, and the like. The compound of formula (II) may be suitable for use in diagnostics for detecting the proteins or peptides which are in direct interaction with the compounds of formula (II).

A method of detecting proteins embodying features of the present invention includes: (a) obtaining a compound of the formula (II); (b) obtaining a sample from a biological fluid; (c) contacting the sample of (b) with the compound of (a); (d) removing unbound sample; and (e) isolating and/or analyzing the binding protein.

In conclusion, the present invention provides methods of treating cancer employing a predetermined derivative of isoxazole. In addition, the present invention provides compounds and methods of using these compounds for isolating and/or detecting a binding protein, which may be indicative of a disease.

The foregoing detailed description and examples have been provided by way of explanation and illustration, and are not intended to limit the scope of the appended claims. Many variations in the presently preferred embodiments illustrated herein will be obvious to one of ordinary skill in the art, and remain within the scope of the appended claims and their equivalents.

The invention claimed is:

1. A method for the treatment of colon cancer, lung cancer, leukemia, Kaposi's sarcoma, ovarian cancer, sarcoma, meningioma, intestinal cancer, cancer of the lymph nodes, brain tumors, breast cancer, stomach cancer, cancer of the pancreas, cancer of the prostate, and skin cancer comprising administering to a patient or an animal in need thereof a therapeutically effective amount of a compound having a formula (I):

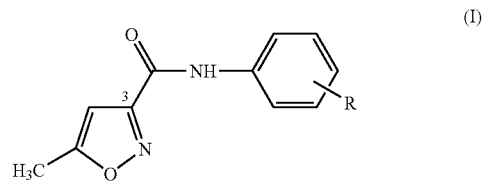

or a physiologically tolerable salt thereof;

wherein R is selected from the group consisting of —H, 2-Cl, 3-Cl, 4-Cl, 2,4-(Cl)₂, 2-F, 3-F, 4-F, 2,4-(F)₂, 2-Br, 3-Br, 4-Br, 2,4-(Br)₂, 2-CF₃, 3-CF₃, 4-CF₃, 2,4-(CF₃)₂, 2-COOH, 3-COOH, 4-COOH, 2,4-(COOH)₂, 2-OCH₃, 3-OCH₃, 4-OCH₃, 3,4,5-(OCH₃)₃, 2-NH—CO—CH₂Cl, 4-NH—CO—CH₂Cl, 2-NH—CO—CH₂Br, 4-NH—CO—CH₂Br, or —CONHCH(COOC₂H₅) CH₂CH₂COOC₂H₅.

2. The method of claim 1 further comprising administering an additional cancer therapeutic agent.

3. The method of claim 2, wherein said additional cancer therapeutic agent is selected from the group consisting of tumor irradiation, a chemotherapeutic agent, an expression construct comprising a nucleic acid encoding a cancer therapeutic gene and a promoter operative in eukaryotic cells, said nucleic acid being operatively linked to said promoter, and combinations thereof.

4. The method of claim 3, wherein said chemotherapeutic agent comprises a DNA damaging agent selected from the group consisting of verapamil, podophyllotoxin, procarbazine, mechlorethamine, cyclophosphamide, camptothecin, ifosfamide, melphalan, chlorambucil, bisulfan, nitrosurea, dactinomycin, daunorubicin, doxorubicin, bleomycin, plicomycin, mitomycin, etoposide (VP16), tamoxifen, taxol, transplatinum, 5-fluorouracil, vincristin, vinblastin, methotrexate, cisplatin, carboplatin, oxaliplatin, and combinations thereof.

5. The method of claim 3, wherein said irradiation is selected from the group consisting of X-ray radiation, UV-radiation, γ-radiation, microwave radiation, and combinations thereof.

* * * * *